US009759697B2

(12) United States Patent
Gras et al.

(10) Patent No.: US 9,759,697 B2
(45) Date of Patent: *Sep. 12, 2017

(54) ANALYTICAL METHOD FOR DETECTING FUEL MARKERS

(71) Applicants: Dow Global Technologies LLC, Midland, MI (US); Rohm and Haas Company, Philadelphia, PA (US)

(72) Inventors: Ronda L. Gras, Edmonton (CA); Jim C. Luong, Sherwood Park (CA); Warren E. Smith, Buckinghamshire (GB)

(73) Assignees: ROHM AND HAAS COMPANY, Philadelphia, PA (US); DOW GLOBAL TECHNOLOGIES LLC, Midland, MI (US)

( * ) Notice: Subject to any disclaimer, the term of this patent is extended or adjusted under 35 U.S.C. 154(b) by 53 days.

This patent is subject to a terminal disclaimer.

(21) Appl. No.: 14/787,520

(22) PCT Filed: May 2, 2014

(86) PCT No.: PCT/US2014/036492
§ 371 (c)(1),
(2) Date: Oct. 28, 2015

(87) PCT Pub. No.: WO2014/179646
PCT Pub. Date: Nov. 6, 2014

(65) Prior Publication Data
US 2016/0077066 A1 Mar. 17, 2016

Related U.S. Application Data

(60) Provisional application No. 61/818,506, filed on May 2, 2013.

(51) Int. Cl.
G01N 30/72 (2006.01)
G01N 33/28 (2006.01)
C10L 1/00 (2006.01)
G01N 30/46 (2006.01)
G01N 30/60 (2006.01)
G01N 30/88 (2006.01)
G01N 30/04 (2006.01)

(52) U.S. Cl.
CPC .......... *G01N 30/7206* (2013.01); *C10L 1/003* (2013.01); *G01N 30/463* (2013.01); *G01N 30/6078* (2013.01); *G01N 30/88* (2013.01); *G01N 33/28* (2013.01); *G01N 33/2882* (2013.01); *G01N 30/465* (2013.01); *G01N 30/7233* (2013.01); *G01N 2030/042* (2013.01); *G01N 2030/8854* (2013.01)

(58) Field of Classification Search
CPC ............. G01N 30/7206; G01N 30/463; G01N 30/6078; G01N 30/88; G01N 33/28; G01N 33/2882; G01N 30/465; G01N 30/7233; G01N 2030/042; G01N 2030/8854; C10L 1/003
USPC .............................................. 73/23.35–23.42
See application file for complete search history.

(56) References Cited

U.S. PATENT DOCUMENTS

| 4,675,454 A | * | 6/1987 | Mossman | ............... | C07C 41/09 568/630 |
| 5,268,302 A | * | 12/1993 | Rounbehler | ........... | G01N 30/84 422/88 |
| 5,492,555 A | | 2/1996 | Strunk et al. | | |
| 5,981,283 A | | 11/1999 | Anderson, II et al. | | |
| 7,858,373 B2 | | 12/2010 | Banavali et al. | | |
| 8,230,719 B2 | * | 7/2012 | Fisher | .................. | G01N 30/463 73/23.36 |
| 8,322,189 B2 | | 12/2012 | Wang | | |

(Continued)

FOREIGN PATENT DOCUMENTS

| CN | 1513118 A | 7/2004 |
| CN | 101012402 A | 8/2007 |

(Continued)

OTHER PUBLICATIONS

Sacks, et al., "Pressure-Tunable Dual-Column Ensembles for High-Speed GC and GC/MS", J. High Resol. Chromatogr, vol. 23, issue 3, pp. 225-234 (2000).
Seeley, "Recent advances in flow-controlled multidimensional gas chromatography", J. Chrom. A, pp. 1-14 (2012).
Sasamoto, et al., "Selectable one-dimensional or two-dimensional gas chromatography-mass spectrometry with simultaneous olfactometry or element-specific detection", J. Chrom. A., vol. 1217 pp. 2903-2910 (2010).
Tranchida, et al., "Heart-cutting multidimensional gas chromatography: A review of recent evolution, applications, and future propspects", Analytica Chimica Acts, vol. 716, pp. 66-75 (2012).

(Continued)

Primary Examiner — Hezron E Williams
Assistant Examiner — Marrit Eyassu
(74) Attorney, Agent, or Firm — Kenneth Crimaldi

(57) ABSTRACT

A gas chromatographic method for detecting a marker compound in a fuel by (a) introducing a sample of fuel into a first capillary column coated with a stationary phase based on polydimethylsiloxane and allowing the sample to flow through the first column to produce a first effluent; (b) allowing the first effluent to pass through a detector and identifying a retention time range in it which includes a retention time of the marker compound; (c) introducing only a portion of the first effluent stream which is within the retention time range into a second capillary column coated with either (i) an ionic sorbent or (ii) a polyethylene glycol, and allowing said portion to flow through the second capillary column to produce a second effluent stream; and (d) allowing the second effluent to pass through a detector; wherein the marker compound has formula $Ar(R^2)_m(OR^1)_n$ and is present in the fuel at a level from 0.01 ppm to 100 ppm.

7 Claims, No Drawings

(56) References Cited

U.S. PATENT DOCUMENTS

| | | | |
|---|---|---|---|
| 2005/0019939 A1* | 1/2005 | Spall | G01N 21/359 436/139 |
| 2007/0039375 A1* | 2/2007 | Chaintreau | G01N 30/463 73/23.41 |
| 2009/0100906 A1 | 4/2009 | Bonne | |
| 2013/0305596 A1* | 11/2013 | Amblard | C10L 1/003 44/411 |
| 2014/0075829 A1 | 3/2014 | Green et al. | |
| 2014/0134746 A1* | 5/2014 | Green | C10L 1/003 436/127 |
| 2014/0298990 A1* | 10/2014 | Fan | G01N 30/463 95/23 |

FOREIGN PATENT DOCUMENTS

| | | |
|---|---|---|
| CN | 102253149 A | 11/2011 |
| WO | 2012107454 A1 | 8/2012 |

\* cited by examiner

ANALYTICAL METHOD FOR DETECTING FUEL MARKERS

This invention relates to an analytical method useful in detecting marker compounds in a complex liquid matrix.

Marking of petroleum hydrocarbons and other fuels and oils with various kinds of chemical markers is well known in the art. A variety of compounds have been used for this purpose, as well as numerous techniques for detection of the markers, e.g., absorption spectroscopy and mass spectrometry. For example, U.S. Pat. No. 7,858,373 discloses the use of a variety of organic compounds for use in marking liquid hydrocarbons and other fuels and oils. Combinations of markers can be used as digital marking systems, with the ratios of amounts forming a code for the marked product. Some marker compounds for these products are difficult to detect in the marked fuel by chromatographic separation. The problem addressed by this invention is to find a method for detecting marker compounds in a complex liquid matrix.

STATEMENT OF INVENTION

The present invention provides a gas chromatographic method for detecting a marker compound in a petroleum hydrocarbon or a liquid biologically derived fuel; said method comprising: (a) introducing a sample of a petroleum hydrocarbon or a liquid biologically derived fuel into a first capillary column which is an open tubular column coated with a polysiloxane stationary phase and allowing the sample to flow through the first capillary column to produce a first effluent stream; (b) allowing the first effluent stream to pass through a detector and identifying a retention time range in the first effluent stream which includes a retention time of the marker compound; (c) introducing only a portion of the first effluent stream which is within the retention time range into a second capillary column which is an open tubular column coated with either (i) an ionic sorbent or (ii) a polyethylene glycol, and allowing said portion to flow through the second capillary column to produce a second effluent stream; and (d) allowing the second effluent stream to pass through a detector;
wherein the marker compound has formula $Ar(R^2)_m(OR^1)_n$, wherein Ar is an aromatic ring system having from six to twenty carbon atoms, $R^1$ is $C_1$-$C_{12}$ alkyl or $C_2$-$C_{12}$ alkenyl, $R^2$ is $C_1$-$C_{12}$ alkyl or $C_3$-$C_{12}$ alkenyl, m is an integer from zero to five and n is an integer from one to three; and wherein each compound of formula $Ar(R^2)_m(OR^1)_n$ is present in the petroleum hydrocarbon or a liquid biologically derived fuel at a level from 0.01 ppm to 100 ppm.

DETAILED DESCRIPTION

Percentages are weight percentages (wt %) and temperatures are in ° C., unless specified otherwise. Boiling points mentioned herein are measured at atmospheric pressure. Concentrations are expressed either in parts per million ("ppm") calculated on a weight/weight basis, or on a weight/volume basis (mg/L); preferably on a weight/volume basis. The term "petroleum hydrocarbon" refers to products having a predominantly hydrocarbon composition, although they may contain minor amounts of oxygen, nitrogen, sulfur or phosphorus; petroleum hydrocarbons include crude oils as well as products derived from petroleum refining processes; they include, for example, crude oil, lubricating oil, hydraulic fluid, brake fluid, gasoline, diesel fuel, kerosene, jet fuel and heating oil. Marker compounds of this invention can be added to a petroleum hydrocarbon or a liquid biologically derived fuel; examples of the latter are biodiesel fuel, ethanol, butanol, ethyl tert-butyl ether or mixtures thereof. A substance is considered a liquid if it is in the liquid state at 20° C. A biodiesel fuel is a biologically derived fuel containing a mixture of fatty acid alkyl esters, especially methyl esters. Biodiesel fuel typically is produced by transesterification of either virgin or recycled vegetable oils, although animal fats may also be used. An ethanol fuel is any fuel containing ethanol, in pure form, or mixed with petroleum hydrocarbons, e.g., "gasohol." An "alkyl" group is a substituted or unsubstituted saturated hydrocarbyl group having from one to twenty-two carbon atoms in a linear, branched or cyclic arrangement. Substitution on alkyl groups of one or more OH or alkoxy groups is permitted; other groups may be permitted when specified elsewhere herein. Preferably, alkyl groups are unsubstituted. Preferably, alkyl groups are linear or branched. An "alkenyl" group is an alkyl group having at least one carbon-carbon double bond. Preferably, alkenyl groups have one or two carbon-carbon double bonds, preferably one. An "aryl" group is a substituent derived from an aromatic hydrocarbon compound. An aryl group has a total of from six to twenty ring atoms, unless otherwise specified, and has one or more rings which are separate or fused. Preferably, the marker compounds contain elements in their naturally occurring isotopic proportions.

A "capillary column" is a column suitable for gas chromatography having an inner diameter from 75 to 750 μm, preferably from 100 to 550 μm, preferably from 150 to 400 μm, preferably from 150 to 350 μm and a length of 5 to 100 m, preferably 7 to 60 m. Preferably, when a mass spectrometer is used as a detector the column diameter is no greater than 400 μm, preferably no greater than 350 μm, preferably no greater than 330 μm. Preferably, capillary columns are made from polyimide-coated fused silica glass or passivated metal. In the present method, the columns are in one or more ovens of the type usually used in gas chromatographs, and the inlets are of the typical configuration; samples are introduced into the columns in an inert carrier gas. Preferably, the amount of sample injected into the gas chromatograph is from 0.2 to 5 μL, preferably from 0.5 to 3 μL, preferably from 0.8 to 2 μL. Preferably the sample is undiluted petroleum hydrocarbon or liquid biologically derived fuel. Preferably the injection is split such that the ratio of total injection to the amount sent to the first column is from 25:1 to 15:1, preferably about 20:1. Preferably, the oven temperature for the first column initially is from 25 to 200° C., preferably from 50 to 150° C., preferably from 40 to 100° C. and then increases to a temperature from 300 to 450° C., preferably from 325 to 425° C., preferably from 350 to 400° C. Preferably, the oven temperature for the second column follows the same profile as that for the first column. Preferably, the carrier gas (preferably helium) flow rate is from 0.2 to 30 mL/min, preferably from 0.5 to 20 mL/min, preferably from 1 to 10 mL/min. Those skilled in the art will appreciate that the parameters mentioned above are interrelated and are not critical individually, but they can be adjusted together to achieve optimum separation of the desired compounds.

A "polysiloxane" stationary phase is one which is based on polydimethylsiloxane. Preferably, the polysiloxane stationary phase is an unsubstituted polydimethylsiloxane or a polydimethylsiloxane substituted with phenyl, cyanopropyl or trifluoromethyl groups; preferably phenyl or cyanopropyl (no greater than 30 mole % substitution of these groups for methyl, preferably no more than 25 mole %, preferably no more than 20 mole %); or a polydimethylsiloxane with embedded aryl groups, preferably phenylene groups (no more than 30 mole %). Preferably, the ionic sorbent is an inorganic salt or a mixture of inorganic salts; preferably sodium or potassium or barium salts or a mixture thereof; preferably sodium sulfate, potassium sulfate, barium sulfate, chlorides of sodium, potassium or barium, or a mixture thereof. Especially preferred ionic sorbents include sodium sulfate, potassium sulfate, barium chloride, barium sulfate or a mixture thereof, preferably barium sulfate or potassium sulfate. Preferably, the polyethylene glycol has a number average molecular weight from 10,000 to 30,000, preferably from 15,000 to 25,000. An especially preferred polyethylene glycol is CARBOWAX 20M. Preferably, when a mass spectrometer is used as a detector, the second column is a polyethylene glycol column.

The effluent from the first capillary column passes through a detector. The detector can be any one capable of detecting the fuel components and the marker; preferably a flame ionization detector (FID), atomic emission detector, pulsed discharge helium ionization detector, dielectric barrier detector, thermal conductivity detector, helium ionization detector, mass selective detector (e.g., a mass spectrometer (MS)); preferably a FID or MS. The retention-time range in which the marker elutes had been determined previously by injection of the marker itself. Typically, the marker (if present) would elute under the peaks due to components of the petroleum hydrocarbon or liquid biologically derived fuel. Preferably the retention time range is wide enough to ensure that the marker would have eluted in this range but narrow enough to avoid sending most of the petroleum hydrocarbon or a liquid biologically derived fuel to the second column. The retention time range will vary depending on oven temperature, flow rate, and column characteristics, but preferably, the retention time range is from 0.1 to 2 minutes, preferably from 0.5 to 1 minute, preferably from 0.1 to 0.3 minutes. The effluent passes through a detector (preferably FID) to confirm that the peaks are consistent with the retention time range containing the marker. The portion of the effluent from the column which elutes during the identified retention time range including the marker is sent to the second capillary column Effluent from the second column passes through at least one detector. In one preferred embodiment a mass spectrometer is used as the detector and also enables identification of the marker compound. In another preferred embodiment a mass spectrometer is not used and the sample is identified using another type of detector (preferably FID or thermal conductivity detector, preferably FID), preferably using internal or external standard techniques or another quantitative method. Any standard switching device suitable for use in gas chromatography can be used to divert the portion of the effluent from the first column which is not introduced into the second column. Preferably a pneumatically activated rotary or slider valve or a non-contact switching valve, preferably a Deans switch is used. Standard splitters suitable for use in gas chromatography such as capillary flow technology or SilFlow planar microfluidic devices can be used to send column effluent to more than one detector simultaneously. Preferably, at least 60 wt % of the first effluent stream is diverted and not introduced into the second column, preferably at least 80 wt %, preferably at least 90 wt %, preferably at least 95 wt %, preferably at least 98 wt %. Preferably, the portion of the first effluent stream that is not sent to the second capillary column is diverted to waste.

Preferably, $R^1$ is linear or branched. Preferably, $R^2$ is linear or branched Preferably, $R^1$ is $C_4$-$C_{12}$ alkyl or $C_4$-$C_{12}$ alkenyl, preferably $C_4$-$C_{12}$ alkyl, preferably $C_4$-$C_{10}$ alkyl. Preferably, $R^2$ is $C_1$-$C_6$ alkyl or $C_3$-$C_6$ alkenyl, preferably $C_1$-$C_6$ alkyl, preferably $C_1$-$C_4$ alkyl, preferably methyl or ethyl. Preferably, n is one or two, preferably one. Preferably, m is from zero to two, preferably zero or one, preferably zero. Preferably, Ar represents a benzene ring system and the compound of formula $Ar(R^2)_m(OR^1)_n$ is described by formula (I)

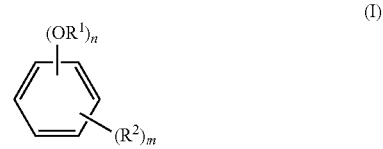

Preferably, in formula (I), $R^1$ is $C_4$-$C_{12}$ alkyl or $C_4$-$C_{12}$ alkenyl, preferably $C_4$-$C_{12}$ alkyl, preferably $C_4$-$C_{10}$ alkyl; preferably $R^2$ is $C_1$-$C_6$ alkyl or $C_3$-$C_6$ alkenyl, preferably $C_1$-$C_6$ alkyl, preferably $C_1$-$C_4$ alkyl, preferably methyl or ethyl. Preferably, in formula (I), m is from zero to two, preferably zero or one, preferably zero; preferably, n is one or two, preferably one. In one preferred embodiment, in formula (I), n is two or three, $R^1$ is methyl, $R^2$ is methyl or is absent (m=0) and m is zero or one; preferably n is two or three, $R^1$ is methyl and m is zero.

In one preferred embodiment, the compound of formula $Ar(R^2)_m(OR^1)_n$ is described by formula (II)

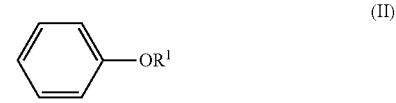

in which $R^1$ is $C_4$-$C_{12}$ alkyl or $C_4$-$C_{12}$ alkenyl, preferably $C_4$-$C_{12}$ alkyl, preferably $C_4$-$C_{10}$ alkyl.

In one preferred embodiment, Ar has from 10 to 12 carbon atoms, n is one or two, $R^1$ is methyl, $R^2$ is methyl or is absent (m=0) and m is zero or one; preferably Ar is a substituted (substituted only by —$OR^1$) biphenyl or naphthalene, n is one or two, $R^1$ is methyl and m is zero.

In using the compounds described herein as markers, preferably the minimum amount of each compound added to a liquid to be marked is at least 0.05 ppm, preferably at least 0.1 ppm, preferably at least 0.2 ppm, preferably at least 0.3 ppm, preferably at least 0.4 ppm, preferably at least 0.5 ppm, preferably at least 1 ppm. Preferably, the maximum amount of each marker is 50 ppm, preferably 20 ppm, preferably 15 ppm, preferably 10 ppm, preferably 8 ppm. Preferably, the maximum total amount of marker compounds is 100 ppm, preferably 70 ppm, preferably 60 ppm, preferably 50 ppm, preferably 40 ppm, preferably 30 ppm, preferably 20 ppm, preferably 16 ppm, preferably 12 ppm, preferably 10 ppm. Preferably, a marker compound is not detectable by visual means in the marked petroleum hydrocarbon or liquid biologically derived fuel, i.e., it is not possible to determine by unaided visual observation of color or other characteristics that it contains a marker compound. Preferably, a marker compound is one that does not occur normally in the petroleum hydrocarbon or liquid biologically derived fuel to which it is added, either as a constituent of the petroleum hydrocarbon or liquid biologically derived fuel itself, or as an additive used therein.

Preferably, the marker compounds have a log P value of at least 3, where P is the 1-octanol/water partition coefficient. Preferably, the marker compounds have a log P of at least 4, preferably at least 5. Log P values which have not been experimentally determined and reported in the literature can be estimated using the method disclosed in Meylan, W. M & Howard, P. H., *J. Pharm. Sci.*, vol. 84, pp. 83-92 (1995). Preferably the petroleum hydrocarbon or liquid biologically derived fuel is a petroleum hydrocarbon, biodiesel fuel or ethanol fuel; preferably a petroleum hydrocarbon or biodiesel fuel; preferably a petroleum hydrocarbon; preferably crude oil, gasoline, diesel fuel, kerosene, jet fuel or heating oil; preferably gasoline or diesel fuel; preferably diesel fuel.

Preferably, more than one marker compound is present. Use of multiple marker compounds facilitates incorporation into the petroleum hydrocarbon or liquid biologically derived fuel of coded information that may be used to identify the origin and other characteristics of the petroleum hydrocarbon or liquid biologically derived fuel. The code comprises the identities and relative amounts, e.g., fixed integer ratios, of the marker compounds. One, two, three or more marker compounds may be used to form the code. Marker compounds according to this invention may be combined with markers of other types, e.g., markers detected by absorption spectrometry, including those disclosed in U.S. Pat. No. 6,811,575; U.S. Pat. App. Pub. No. 2004/0250469 and EP App. Pub. No. 1,479,749. Marker compounds are placed in the petroleum hydrocarbon or liquid biologically derived fuel directly, or alternatively, placed in an additives package containing other compounds, e.g., antiwear additives for lubricants, detergents for gasoline, etc., and the additives package is added to the petroleum hydrocarbon or liquid biologically derived fuel. Use of more than one marker may be useful to avoid removal of a marker by distillation. Preferably, at least two markers are used which differ in boiling point by at least 50° C., preferably at least 75° C., preferably at least 100° C., preferably at least 125° C.

The marker compounds may be prepared by methods known in the art, e.g., allowing an aryloxide salt to react with an alkyl halide to form an aryl alkyl ether.

EXAMPLES

Analytical Studies
Separation of Fuel Markers from Fuel Matrix Using Single Dimensional Gas Chromatography Methodologies:

Gas Chromatography/Mass Spectrometry (GC/MS): The GC retention times of all three dimethoxybenzene isomers, all 3 trimethoxybenzene isomers, and butyl phenyl ether were compared to that of the 50 volume % diesel distillate using the following GC columns: DB-5, DB-35, DB-210, and DB-WAX. With every column, the marker co-elutes with components in the matrix, i.e., the retention time of each candidate marker was within the retention time of the fuel matrix. Insufficient separation was obtained in each case.

Thermionic Detection (TID): This detector is sensitive to nitrogen-containing compounds (e.g., amines and nitro compounds), and is used to detect them in the presence of non-nitrogen containing compounds. It was possible to detect all of the candidate markers in a fuel matrix at high (% level) concentrations. However, only the 1,2,4-trimethoxy benzene could be detected at levels as low as 10 ppm in the diesel distillate matrix. Nitrocyclohexane could not be detected at this level.
Separation of Fuel Markers from Fuel Matrix Using Multi-Dimensional Gas Chromatography and Mass Spectrometry with Either GC-GC-MS or GC×GC-MS The ability to identify/separate 1,2-dimethoxy benzene (veratrole), 1,3,5-trimethoxy benzene, and butyl phenyl ether in ESSO Canada and FASTGAS diesel fuels was evaluated at the GC Center of Expertise Analytical Tech Center, Dow Chemical Canada.
Three methods were evaluated:
1) Conventional Two Dimensional Gas Chromatography (GC-GC/FID)
    First dimension GC column: 30 m×0.25 mm×0.25 μm DB-5 ms UI (WCOT)
    Second dimension GC column: 10 m×0.53 mm id CP-Lowox (Ionic sorbent/PLOT)
2) Pulsed Flow Modulated Comprehensive Two-dimensional GC (PFM-GC×GC/FID)
    First dimension GC column: 20 m×0.18 mm×0.4 μm polydimethylsiloxane (DB-1, WCOT)
    Second dimension GC column: 5 m×0.25 mm×0.15 μm HP-Innowax (WCOT)
3) Conventional Two-dimensional Gas Chromatography with MS (GC-GC/MSD in SCAN/SIM mode)
    First dimension GC column: 15 m×0.25 mm×0.1 μm polydimethysiloxane (DB-1HT, WCOT)
    Second dimension GC column: 23 m×0.25 mm×1 μm, stationary phase: polyethylene glycol 20,000 (VF-WAXms)

While all three methods studied can separate the compounds from the matrix, the best results were obtained using method 3 which offers a high degree of selectivity and sensitivity as well as structural elucidation capability. All three of the candidates could be separated from the diesel fuel matrices, with detection limits in the 100 ppb range or lower. The statistics on a preliminary data set comprising 7 analyses indicated a relative standard deviation of detection of under 4%.

D) Distillation/Detection in Fuel Distillates
A sample of diesel fuel was marked with 10 ppm butylphenyl ether, 10 ppm 1,2-dimethoxybenzene and 2.5 ppm ACCUTRACE 3,4-10 marker. The fuel was distilled in accordance with ASTM D-86 procedure, except that the distillation was stopped after 50% by volume of the initial charge had been distilled overhead. The overhead distillation temperature reached approximately 280° C. by the end of the experiment. Four samples, as shown below, were analyzed for the presence/absence of the markers. Based on the boiling characteristics of the markers, we anticipate Sample C to contain the vast majority of the butylphenyl ether and 1,2-dimethoxybenzene, and essentially no ACCUTRACE 3,4-10 marker. We also anticipate Sample D to contain very little butylphenyl ether or 1,2-dimethoxybenzene, and it should contain essentially all of the ACCUTRACE 3,4-10 marker.
    Sample A—Virgin diesel fuel
    Sample B—Virgin diesel fuel marked with 10 ppm butylphenyl ether, 10 ppm 1,2-dimethoxybenzene, and 2.5 ppm ACCUTRACE 3,4-10 marker
    A 700 mL aliquot of Sample B was distilled using a variant of ASTM D-86 procedures resulting in 2 nearly equal fractions (by volume), and these are:
    Sample C—overhead distillate, $1^{st}$ 50% of the volatiles
    Sample D—distillate residue, $2^{nd}$ 50% of the volatiles (not taken overhead in this experiment).
When the samples were analyzed using the GC-GC/MSD in selective ion monitoring (SIM) technique, the following results were obtained:

| Analytical Results (ppm) | BPE | BPE2 | DMB | DMB2 |
| --- | --- | --- | --- | --- |
| Virgin diesel (Sample A) | ND | ND | ND | ND |
| Marked diesel (Sample B) | 10.0 | 10.0 | 10.0 | 10.0 |
| 50% OVHS, distilled (Sample C) | 20.2 | 20.6 | 20.7 | 20.6 |
| Distillate residues (Sample D) | 0.1 | 0.1 | ND | ND |

BPE = Butyl Phenyl Ether
DMB = 1,2-Dimethoxybenzene
ND = not detected, detection limit: ca 50 ppb Demonstration of Marker Distillation Across Diesel Fuel Boiling Range An equimolar mixture of hexylphenyl ether, octylphenyl ether and decylphenyl ether standard was prepared via the standard Williamson ether technique. Diesel fuel was spiked with the mixture above to obtain approximately 10 ppm of each marker in the fuel. 10 ppm butyl phenyl ether was added to the fuel as well.

Following the ASTM D-86 protocol modified for available laboratory equipment, the diesel fuel was then distilled into 4 fractions of approximately equal mass:

| Fraction | Boiling Range |
| --- | --- |
| First 25% overheads | 170-235° C. |
| $2^{nd}$ 25% overheads | 235-274° C. |
| $3^{rd}$ 25% overheads | 274-303° C. |
| Pot residue | >303° C. |

These 4 fuel samples were then analyzed using a GC-GC-FID technique, with a polydimethylsiloxane first column (DB-5 ms UI, Agilent Technologies) and an ionic second column (CP-Lowox, Agilent Technologies). The peak areas for each marker were normalized to 100%, and the relative amount of marker appearing in the various fractions was calculated. The results are collected in the table:

| Fraction # | butyl phenyl ether BP = 210° C. | hexyl phenyl ether BP = 240° C. | octyl phenyl ether BP = 285° C. | decyl phenyl ether BP = 318° C. |
| --- | --- | --- | --- | --- |
| Fraction 1 | 62.4% | 25.2% | 9.3% | ND |
| Fraction 2 | 35.9% | 49.6% | 28.5% | 29.3% |
| Fraction 3 | 1.7% | 24.4% | 46.4% | 32.3% |
| Pot Residue | ND | 0.8% | 15.9% | 38.4% |

ND means <50 ppb

As can be seen from the data, both hexylphenyl ether and octylphenyl ether were clearly present in all fractions. Butylphenyl ether had been completely removed from the pot residue (bottoms) and the decylphenyl ether did not distill into the lightest fraction. Thus any one of the butyl-, hexyl- and octylphenyl ethers could be added to diesel fuel, and all distillation fractions could be identified as containing the marker system.

The invention claimed is:

1. A gas chromatographic method for detecting a marker compound in a petroleum hydrocarbon or a liquid biologically derived fuel; said method comprising:
   (a) introducing a sample of a petroleum hydrocarbon or a liquid biologically derived fuel into a first capillary column which is an open tubular column coated with a polysiloxane stationary phase and allowing the sample to flow through the first capillary column to produce a first effluent stream; (b) allowing the first effluent stream to pass through a detector and identifying a retention time range in the first effluent stream which includes a retention time of the marker compound; (c) introducing only a portion of the first effluent stream which is within the retention time range into a second capillary column which is an open tubular column coated with either (i) an ionic sorbent or (ii) a polyethylene glycol, and allowing said portion to flow through the second capillary column to produce a second effluent stream; and (d) allowing the second effluent stream to pass through a detector;
   wherein the marker compound has formula (I)

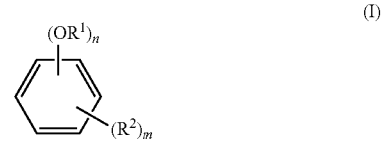

wherein $R^1$ is $C_1$-$C_{12}$ alkyl or $C_2$-$C_{12}$ alkenyl, $R^2$ is $C_1$-$C_{12}$ alkyl or $C_3$-$C_{12}$ alkenyl, m is an integer from zero to five and n is an integer from one to three; and wherein each compound of formula (I) is present in the petroleum hydrocarbon or a liquid biologically derived fuel at a level from 0.01 ppm to 100 ppm.

2. The method of claim 1 in which a portion of the first effluent stream which is not within the retention time range is diverted from the second capillary column using a non-contact switching device.

3. The method of claim 2 in which $R^1$ is $C_4$-$C_{12}$ alkyl.

4. The method of claim 3 in which the marker compound is identified in the second effluent stream by mass spectrometry.

5. The method of claim 4 in which n is one and m is zero.

6. The method of claim 5 in which the second capillary column is coated with an ionic sorbent which is a salt of sodium, potassium or barium, or a mixture thereof.

7. The method of claim 6 in which the polysiloxane stationary phase is polydimethylsiloxane.

* * * * *